US011293873B2

(12) United States Patent
Ferrara, Jr. et al.

(10) Patent No.: US 11,293,873 B2
(45) Date of Patent: Apr. 5, 2022

(54) METHODS AND DEVICES FOR IMPROVED ACCURACY OF TEST RESULTS

(71) Applicant: Xerox Corporation, Norwalk, CT (US)

(72) Inventors: Joseph M. Ferrara, Jr., Webster, NY (US); Erwin Ruiz, Rochester, NY (US); Martin L. Frachioni, Rochester, NY (US)

(73) Assignee: XEROX CORPORATION, Norwalk, CT (US)

( * ) Notice: Subject to any disclaimer, the term of this patent is extended or adjusted under 35 U.S.C. 154(b) by 482 days.

(21) Appl. No.: 14/847,356

(22) Filed: Sep. 8, 2015

(65) Prior Publication Data

US 2017/0067832 A1 Mar. 9, 2017

(51) Int. Cl.
G01N 21/78 (2006.01)
G01N 33/52 (2006.01)
G01N 21/84 (2006.01)
G01N 21/77 (2006.01)
G01N 21/75 (2006.01)

(52) U.S. Cl.
CPC ......... *G01N 21/78* (2013.01); *G01N 21/8483* (2013.01); *G01N 33/52* (2013.01); *G01N 2021/752* (2013.01); *G01N 2021/7793* (2013.01); *G01N 2021/8488* (2013.01)

(58) Field of Classification Search
CPC .... G01N 21/78; G01N 21/8483; G01N 33/52; G01N 2021/752; G01N 2021/7793; G01N 2021/8488
See application file for complete search history.

(56) References Cited

U.S. PATENT DOCUMENTS

| 5,260,219 A * | 11/1993 | Fritz | A61B 5/00 435/12 |
| 7,723,120 B2 * | 5/2010 | Xiao | B01L 3/50273 137/375 |
| 2012/0063652 A1 * | 3/2012 | Chen | G01N 21/274 382/128 |

* cited by examiner

Primary Examiner — Robert J Eom
(74) Attorney, Agent, or Firm — Fay Sharpe LLP

(57) ABSTRACT

The present disclosure relates to using color calibration to improve and increase the accuracy of interpreting color-sensitive results from test strips made of substrates like paper. This is accomplished via a diagnostic test unit including a substrate, at least one region on the substrate, a reagent placed within the region to react, and a series of color legends on the substrate. Different reagent samples may be placed on the separate regions of a substrate for testing. An imaging device is used to capture the reaction results. More precise readings can be obtained by comparing the reaction results to the color legends to determine the measured property of the analyte.

14 Claims, 11 Drawing Sheets

METHODS AND DEVICES FOR IMPROVED ACCURACY OF TEST RESULTS

BACKGROUND

The present disclosure relates generally to methods for automated processing of test units and determination of values for measurements which are based on differences in color. Reading accuracy can be enhanced by use of test units having color legends as described herein, because those color legends can be used as a calibration metric. This finds particular application in testing of various biological fluids, and will be described with particular reference thereto.

Paper-based chemical assay test units generally are formed from a paper substrate, fluid channels and other fluid structures formed on the substrate using wax, and one or more reagents. These test units can be used for analyzing a multitude of samples, depending on the type of reagent that is added to the test strip. Common examples of paper-based chemical assay tests include test units for performing biochemical assays and diagnostics for test fluids such as blood, urine, and saliva. These test units can also be used to measure properties such as water quality, pH value, or the LDL cholesterol level. Such devices can be small, light weight, and low cost, and have applications in fields like healthcare, military, and homeland security.

Most color-based tests are analyzed using a standardized image set for a grading rubric (SIR) that shows certain colors that correspond to a specific value. These values are discontinuous and do not always give the most accurate readings. In addition, such value readings are subjective as the observer must discern which color matches the reading most accurately. Sometimes, a user must manually compare the resulting colors of the test to a set of colors on a reference card, which is not user-friendly or reliable or reproducible.

It would be desirable to provide test units and processing methods that can improve the reading accuracy of test results of an automated program for reading such test results.

BRIEF DESCRIPTION

The present disclosure relates to test units and processing methods that can increase the accuracy of computerized programs that will read the color results of color-based tests. Briefly, the test unit includes one or more color legends that correspond to the potential color results that can occur when a reagent reacts with an analyte. When an image of the test result is taken using an imaging device such as a smart phone, a tablet, or a scanner, the color legend and the color result are equally affected. The computerized program can then use this information to determine the value corresponding to the color result, or provide feedback that a new image must be captured or the test must be performed again.

Disclosed herein in various embodiments are diagnostic test units for measuring a property of a bodily fluid, comprising: a substrate; at least one analytical region on the substrate, each analytical region containing a reagent; and a plurality of color legends on the substrate, each color legend comprising a color range corresponding to the colors that can appear when the reagent reacts with an associated analyte.

Each analytical region may include a microfluidic structure. In some embodiments, there is only one analytical region on the substrate.

In some embodiments, the color legends extend in different directions relative to each other.

In certain embodiments, the test unit has a total of four analytical regions present on the substrate, and the four regions are arranged in a rectangle.

In other embodiments, the test unit has a substrate that is rectangular, a total of four analytical regions are present on the substrate and arranged in a circle, and the unit has a total of four color legends, wherein the four legends form a perimeter suurounding the four analytical regions.

In different embodiments, the test unit has a substrate that is rectangular, a total of four analytical regions are present on the substrate and arranged in a rectangle, and the unit has a total of two color legends, wherein the two color legends are placed on opposite sides of the substrate.

In still other test units, the substrate is rectangular, and the unit has a total of four color legends, wherein first ends of the four legends intersect at a common point on the substrate.

In particular embodiments, each color legend comprises a color range from red to violet, or from red to green.

Some test units may further comprise a handling area on one side of the substrate.

Also disclosed herein are methods of more accurately measuring a property of a bodily fluid, comprising: receiving a test unit comprising a substrate, at least one analytical region on the substrate, each region containing a reagent, and a plurality of color legends on the substrate, each color legend comprising a color range corresponding to the colors that can appear when the reagent reacts with an associated analyte; placing the analyte on the at least one analytical region of the substrate; permitting a reaction to occur; capturing an image of the at least one analytical region after the reaction with an imaging device; and comparing the color of the reacted analytical region in the captured image to the color legend in the captured image to determine a value for the property of the bodily fluid.

The imaging device may be a smart phone or tablet. Blood, water, or saliva may be the bodily fluid placed on the analytical region to react with the reagent. The pH value, the LDL cholesterol level, or the glucose level may be the property of the bodily fluid that is measured.

These and other non-limiting characteristics are more particularly described below.

BRIEF DESCRIPTION OF THE DRAWINGS

The following is a brief description of the drawings, which are presented for the purpose of illustrating the exemplary embodiments disclosed herein and not for the purpose of limiting the same.

DETAILED DESCRIPTION

Figure 1:
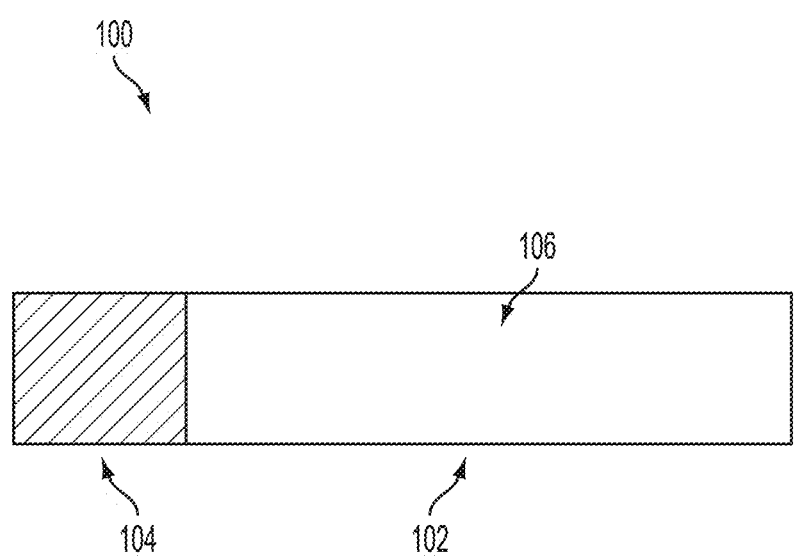
FIG. 1 is a perspective view of a generic testing device.

A more complete understanding of the components, processes, and apparatuses disclosed herein can be obtained by reference to the accompanying drawings. These figures are merely schematic representations based on convenience and the ease of demonstrating the present disclosure, and are, therefore, not intended to indicate relative size and dimensions of the devices or components thereof and/or to define or limit the scope of the exemplary embodiments.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The singular forms "a," "an," and "the" include plural referents unless the context clearly dictates otherwise.

As used in the specification and in the claims, the term "comprising" may include the embodiments "consisting of" and "consisting essentially of." The terms "comprise(s)," "include(s)," "having," "has," "can," "contain(s)," and variants thereof, as used herein, are intended to be open-ended transitional phrases, terms, or words that require the presence of the named components/steps and permit the presence of other components/steps. However, such description should be construed as also describing compositions or processes as "consisting of" and "consisting essentially of" the enumerated components/steps, which allows the presence of only the named components/steps, and excludes other components/steps.

All ranges disclosed herein are inclusive of the recited endpoint and independently combinable (for example, the range of "from 2 watts to 10 watts" is inclusive of the endpoints, 2 watts and 10 watts, and all the intermediate values). Numerical values should be understood to include numerical values which are the same when reduced to the same number of significant figures and numerical values which differ from the stated value by less than the experimental error of conventional measurement technique of the type described in the present application to determine the value.

As used herein, approximating language may be applied to modify any quantitative representation that may vary without resulting in a change in the basic function to which it is related. Accordingly, a value modified by a term or terms, such as "about" and "substantially," may not be limited to the precise value specified. The modifier "about" should also be considered as disclosing the range defined by the absolute values of the two endpoints. For example, the expression "from about 2 to about 4" also discloses the range "from 2 to 4."

One method of measuring colors is the CIELAB color space. This color space uses three dimensions, $L^*$, $a^*$, and $b^*$. $L^*$ is the lightness or L-value, and can be used as a measure of the amount of light transmission through the polycarbonate resin. The values for $L^*$ range from 0 (black) to 100 (diffuse white). The dimension $a^*$ is a measure of the color between magenta (positive values) and green (negative values). The dimension $b^*$ is a measure of the color between yellow (positive values) and blue (negative values), and may also be referred to as measuring the blueness of the color or as the b-value.

Some colors are referred to herein. "Red" has a wavelength of about 620 nanometers to about 740 nm. "Violet" has a wavelength of about 380 nm to about 450 nm. "Green" has a wavelength of about 495 nm to about 570 nm.

The present disclosure relates to testing units used for determining the value of various analytes using color-based test results. Such values can be difficult to objectively and reproducibly determine. It would be desirable to determine such values/measurements/results with a higher degree of accuracy. As previously mentioned, most color-based tests are analyzed using a standardized image set for a grading rubric (SIR) that shows certain colors that correspond to a specific value. Especially in impoverished areas where efforts to bring health care and medicine are in initial phases, it would be desirable to use lower-cost devices such as smartphones for interpreting these color-based test results. However, the cameras in smartphones do not always have the greatest color accuracy, and are generally not calibrated with the test unit either. Thus, the test units of the present disclosure contain a color legend which provides for calibration of the results. The color legend is generated from a large sample size, and any disconnected points can be interpolated. Any inaccuracies which result from the uncalibrated camera should thus affect both the color-based test result and the color legend to an equal degree. This should also be more accurate than comparing the test result to a disconnected legend which has not been affected by the uncalibrated camera. This should also provide a faster way to analyze samples, compared to sending the samples to a distant lab. In addition, to mitigate uniformity issues, multiple color legends can be placed to form a perimeter on the test unit surrounding the analytical regions of the test unit. A picture can be taken of the test unit in multiple orientations, and if a good reading cannot be captured, then the device can provide feedback stating that a new sample needs to be collected.

FIG. 1 is an illustration of a conventional testing device 100. The device includes a rectangular substrate 102 having an analytical region 104 at one end upon which a reagent is located. The remaining portion 106 of the substrate is present to provide a handling area for the user to touch. A bodily fluid, such as blood, urine, or saliva, can be deposited onto the analytical region, or the analytical region can be dipped into the bodily fluid. The reagent reacts with any analyte present in the bodily fluid and changes color, reflecting a value of the analyte (e.g. concentration) or a property of the bodily fluid (e.g. pH).

Figure 2:
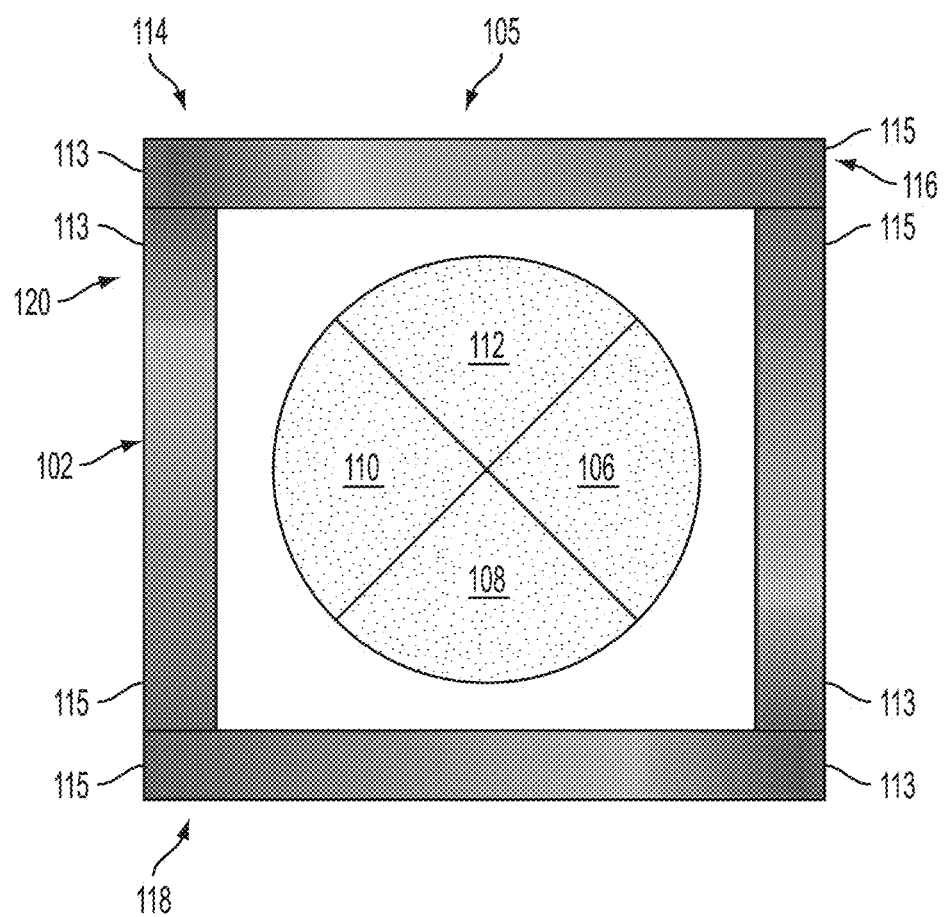
FIG. 2 is a plan view of a square substrate with four regions and four color legends along the perimeter of the substrate, in accordance with one exemplary embodiment of the disclosure.

FIG. 2 is a plan view of an illustrative embodiment of a test unit of the present disclosure. This test unit 105 includes a rectangular substrate 102, which is seen here as having a square shape. The shape of the substrate is not particularly limited, and could be any other suitable shape. For example, other shapes contemplated by the present disclosure include, but are not limited to triangular, hexagonal, or octagonal shapes for the substrate.

A variety of materials are suitable for the substrate. For example, the substrate may be made of paper, polymers, or fabrics, as desired. Desirably, the substrate is hydrophilic to promote absorption of the bodily fluid. Preferably, the substrate requires minimum sample sizes, absorbs the sample quickly, distributes the sample uniformly to the microfluidic structure, and does not interfere with the chemistry during the reaction between reagent and analyte. Of course, cost is a practical consideration, as well. In particularly desirable embodiments, the substrate is made of paper.

The substrate 102 includes a circular portion around the center of the substrate. This circular portion is divided into four analytical regions 106, 108, 110, and 112. Each analytical region is a sector of the circle, and each region contains a microfluidic structure and a reagent which can react with a desired analyte. The microfluidic structure is generally made of a hydrophobic substance (e.g. wax) which is used to create and separate (I.e. divide) various fluidic components such as test regions, fluid entrances, transport channels, etc.

Here, the circular portion is divided into four quadrants. However, the substrate can include only one analytical region, or as many analytical regions as may be desired. This might depend, for example, on the number of samples that are to be imaged and interpreted together. Multiple analytical regions on a substrate allow for more samples to be tested on one device, which may increase the efficiency of the substrate.

In FIG. 2, four color legends 114, 116, 118, and 120 are present on the substrate 102. The color legends form a perimeter around the analytical regions. The color legends of the test unit should span the entire range of colors that can appear when the analyte reacts with the reagent. The color that is produced by the reaction of the analyte with the reagent is referred to herein as the "color result". For example, each color legend may span a range from red to violet, or from red to green, depending the possible resulting values for the color result. As seen here, each color legend has a first end 113 and a second end 115, with the first end of each color legend corresponding to one end of the color range (e.g. red) and the second end of each color legend corresponding to the other end of the color range (e.g. violet or green). First ends of different color legends can be placed adjacent to each other, or the first end of one color legend can be placed adjacent to the second end of another color legend. It is contemplated that this arrangement provides the imaging device with additional points for comparison of the color legend to the color result, even at different orientations of the test unit relative to the imaging device.

As will be seen further herein, the number of color legends may vary as desired, for example depending on the shape of the substrate. Furthermore, the placement of the color legends on the substrate may also vary. For example, the color legends may be placed on opposite sides of the substrate. In some other instances, the color legends may overlap each other.

Figure 3:
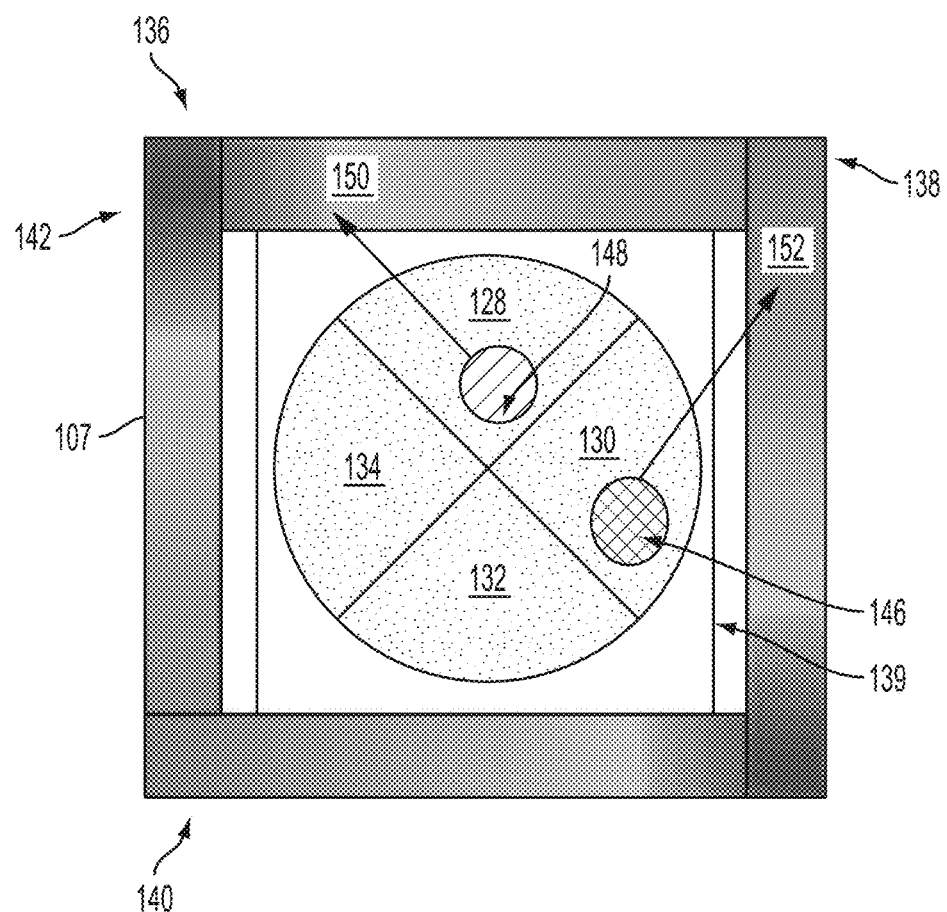
FIG. 3 is a plan view showing a square substrate in which two different samples have been placed in different regions and resulted in different color results, which can then be compared to a color legend, according to another embodiment of the present disclosure.

FIG. 3 is an illustrative diagram showing how the test unit 105 can be used. While this discussion refers particularly to blood as the bodily fluid, it should be appreciated that the testing device is also applicable to a wide variety of other bodily fluids, including urine or saliva.

In FIG. 3, the test unit 105 includes a square substrate 139 having four analytical regions 128, 130, 132, 134 thereon. Four color legends 136, 138, 140, and 142 form a perimeter 107 on the substrate, and the color legends surround the analytical regions. All analytical regions contain the same reagent. Different fluid samples 146 and 148 are placed on regions 128 and 130. The reagent reacts with the samples 146 and 148 to cause a detectable color change (i.e. the color result). The color result of a given sample may then be matched with the corresponding color 150 and 152 on the color legend 142, 138 closest to the sample.

Figure 4:
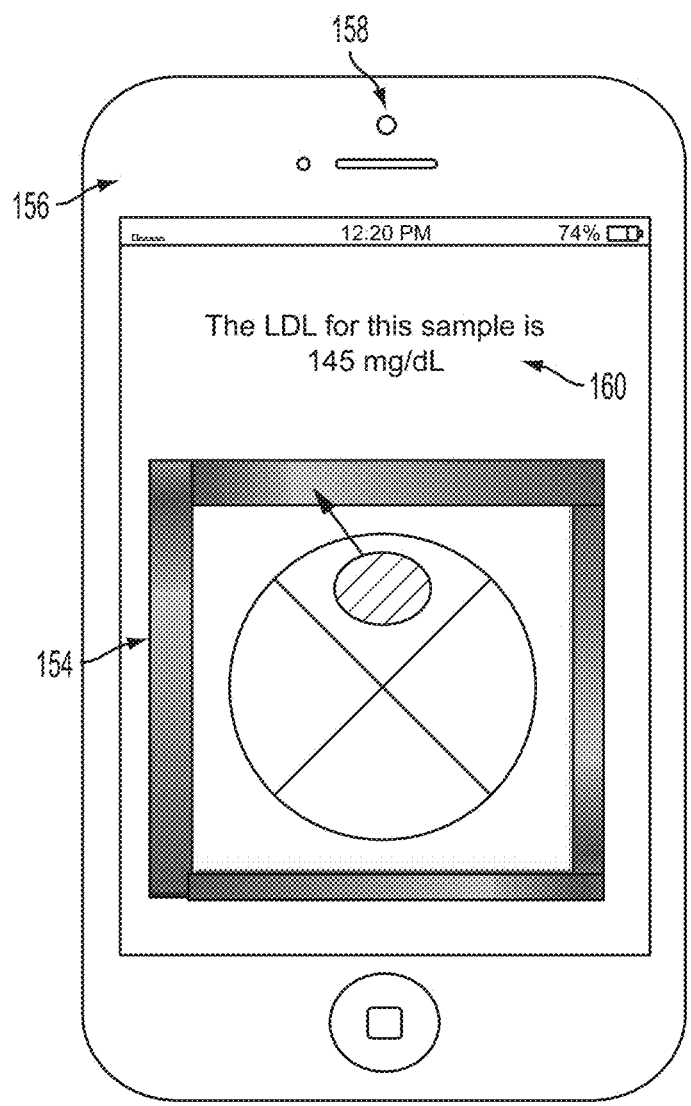
FIG. 4 is an illustrative screenshot view of an imaging device that has been used to capture the color result after the reaction of an analyte and a reagent, showing the determination of the value of a property (LDL level) of the biological fluid using the imaging device.

FIG. 4 is a screenshot view illustrating the use of an imaging device 156 that includes a camera 158 to interpret the color result. The camera 158 is used to take an image of the test device 154 after the sample has reacted. Multiple images of the same substrate may be taken with the imaging device at multiple orientations, to provide the imaging software with different data (e.g. the degree and direction of ambient light, luminance, hue, saturation, etc.) which might affect the interpretation of the color result. The imaging device then reports the value corresponding to the color result. FIG. 4 illustrates the LDL cholesterol level 160 for the sample. Again, the testing device is also applicable to the detection of a wide variety of other medical tests including, but not limited to, testing for the presence of glucose or pH value or other desired information. It is particularly contemplated that the imaging device is a smartphone which is equipped to take color images. However, the imaging device may also be a tablet, a laptop, or a high-density scanner.

Figure 5:
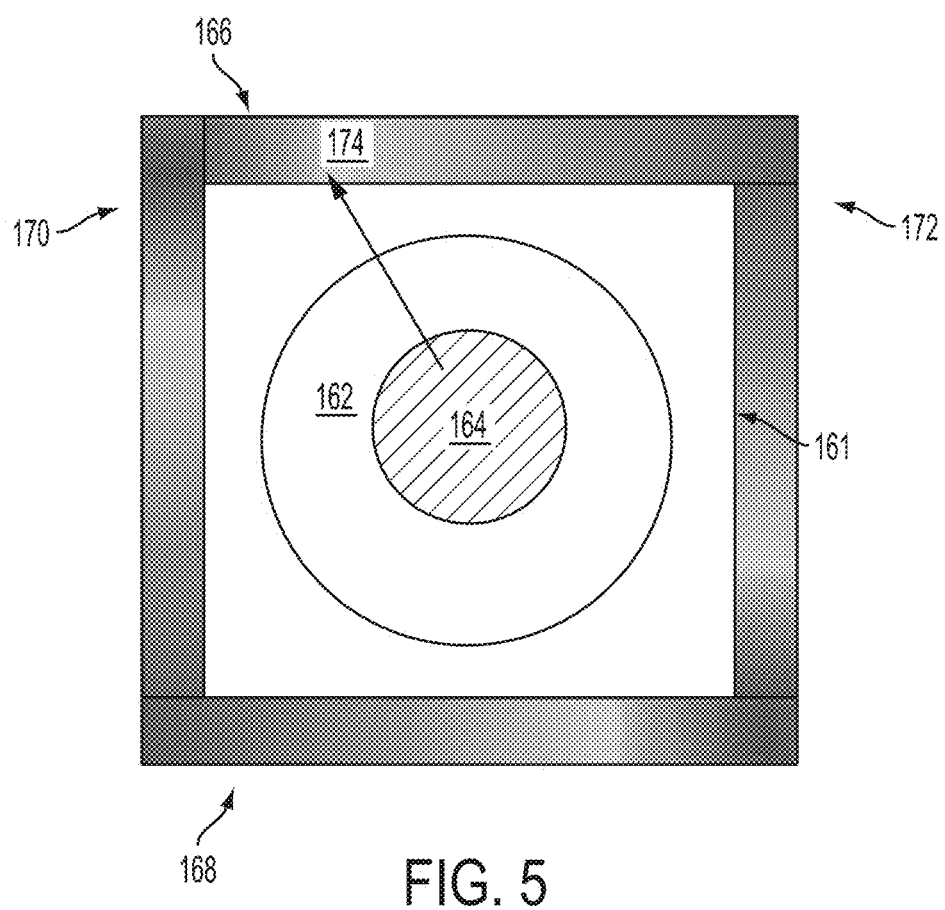
FIG. 5 is a plan view of a square substrate with one large circular region and four color legends in accordance with another embodiment of the disclosure.

FIGS. 5-11 illustrate several different exemplary embodiments of the test unit according to the present disclosure. FIG. 5 illustrates a testing device with a square substrate 161. Only one analytical region 162 is present in this embodiment, and four color legends 166, 168, 170, 172 are present forming a perimeter on the substrate around the analytical region. A bodily fluid sample 164 is placed within the analytical region 162, and the reagent present in the analytical region reacts with analyte present in the sample 164 to cause a detectable color change. The color result of the sample is then matched with the corresponding color 174 on one of the color legends 166.

Figure 6:
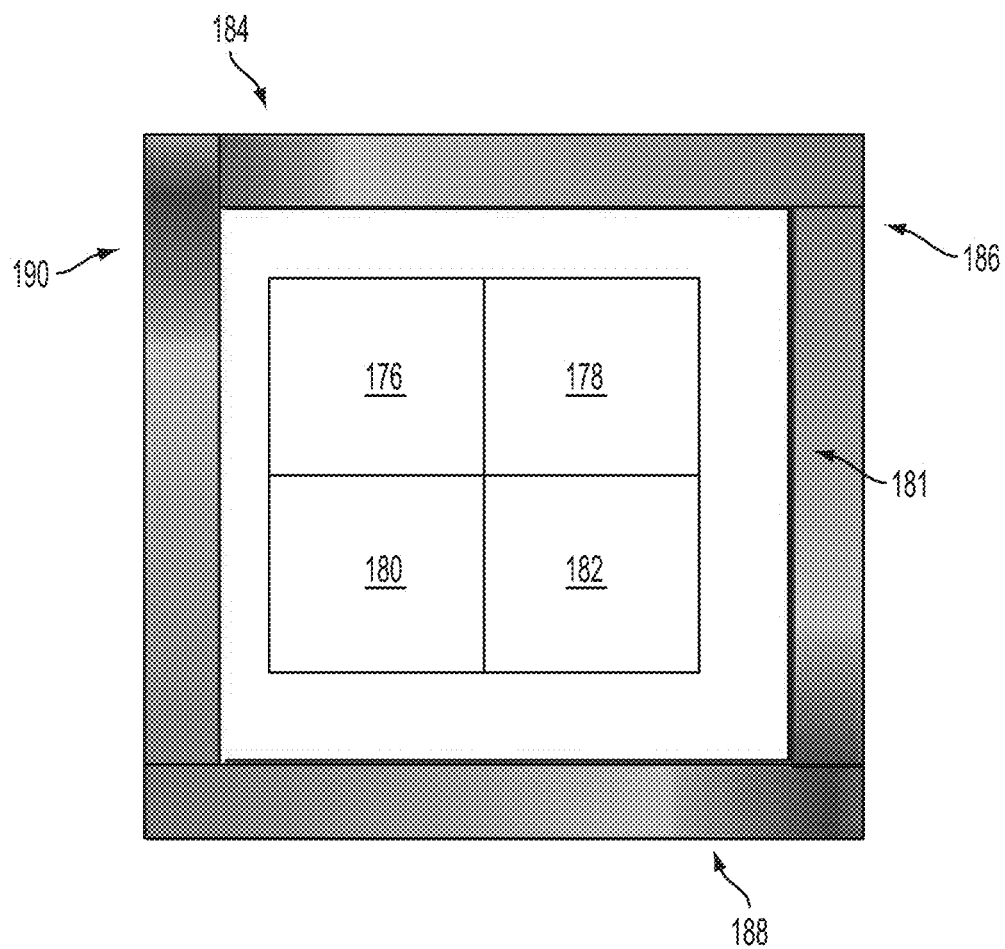
FIG. 6 is a plan view of a square substrate with four square regions and four color legends in accordance with another embodiment of the disclosure.

FIG. 6 illustrates a rectangular substrate 181 having four analytical regions 176, 178, 180, 182. Four color legends 184, 186, 188, 190 are placed around the perimeter of the substrate, each color legend parallel to one side of the substrate. The color legends surround the analytical regions. Here, the analytical regions are rectangular in shape.

Figure 7:
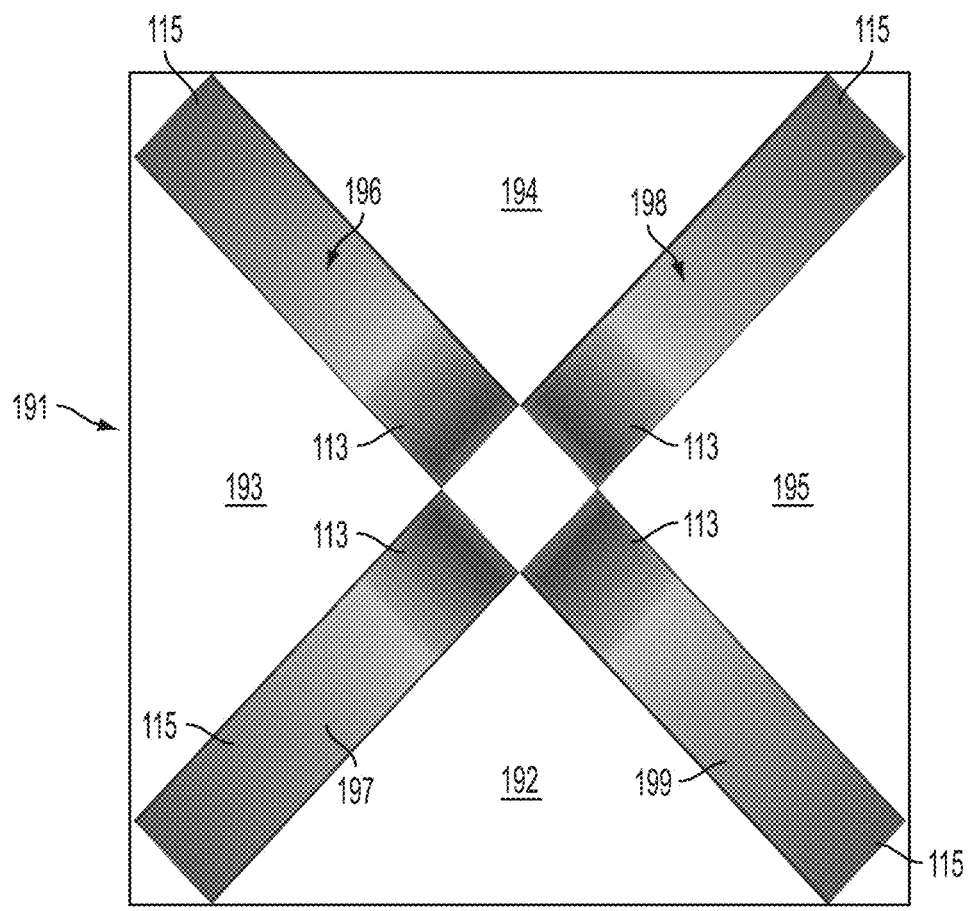
FIG. 7 is a plan view of a square substrate with two color legends intersecting at the center of the substrate. Four regions are located in the triangular areas between the color legends.

FIG. 7 illustrates a testing device having a rectangular substrate 191. In this embodiment, the four color legends 184, 186, 188, 190 are not present on the perimeter of the substrate. Instead, the four color legends are placed diagonally such that their first ends 113 meet at a common point of the substrate 197, and their second ends 115 are located near the corners of the substrate 191. Four analytical regions 192, 193, 194, 195 are then located in the triangular areas between the two color legends 196, 198 and the perimeter 107 of the substrate.

Figure 8:
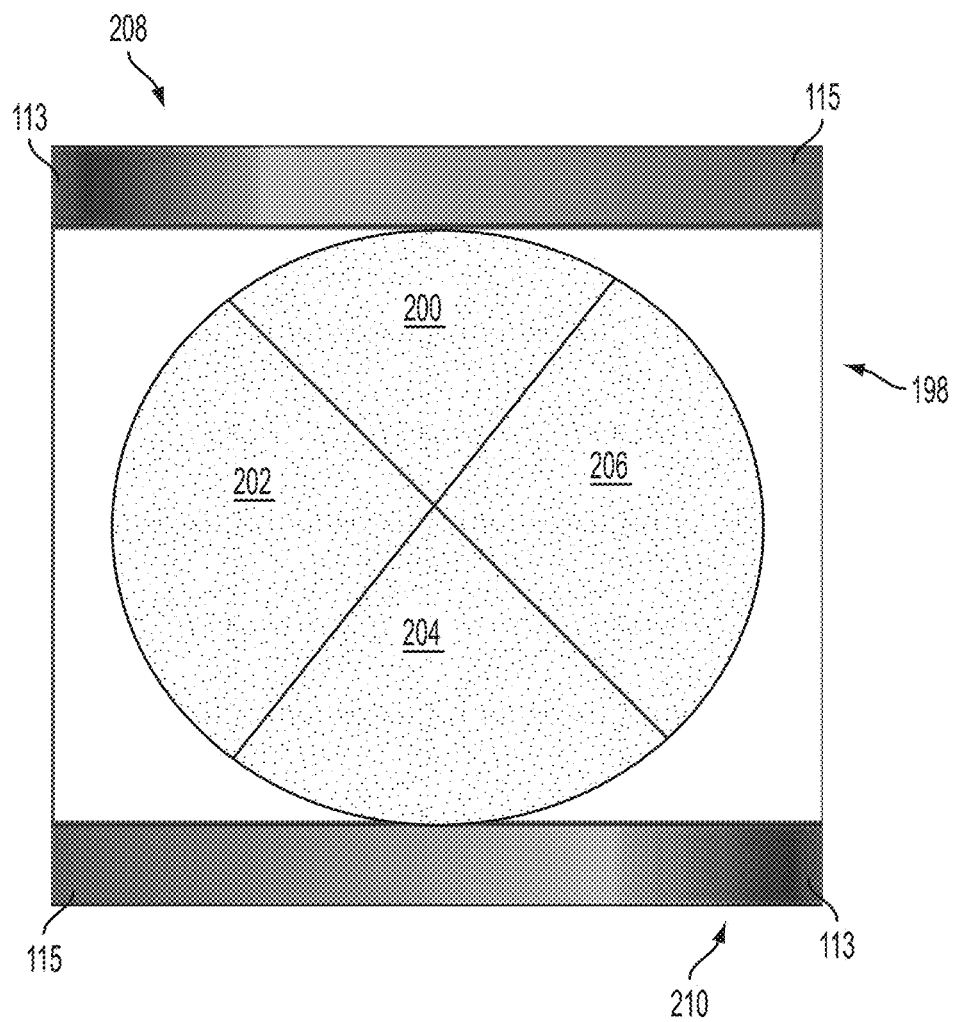
FIG. 8 is a plan view of a square substrate with four arcuate quadrants (i.e. circular sectors) and two color legends on opposite sides of the substrate, in accordance with another embodiment of the disclosure.

FIG. 8 illustrates another testing device with a rectangular substrate 198. Here, only two color legends 208, 210 are present, placed on opposite sides of the substrate 198. It is noted that the color legends are oriented so that that the first ends 113 of the color legends are located at opposite corners/ends of the substrate. Four wedge-shaped analytical regions 200, 202, 204, 206 are present on the substrate, surrounded by the color legends.

Figure 9:
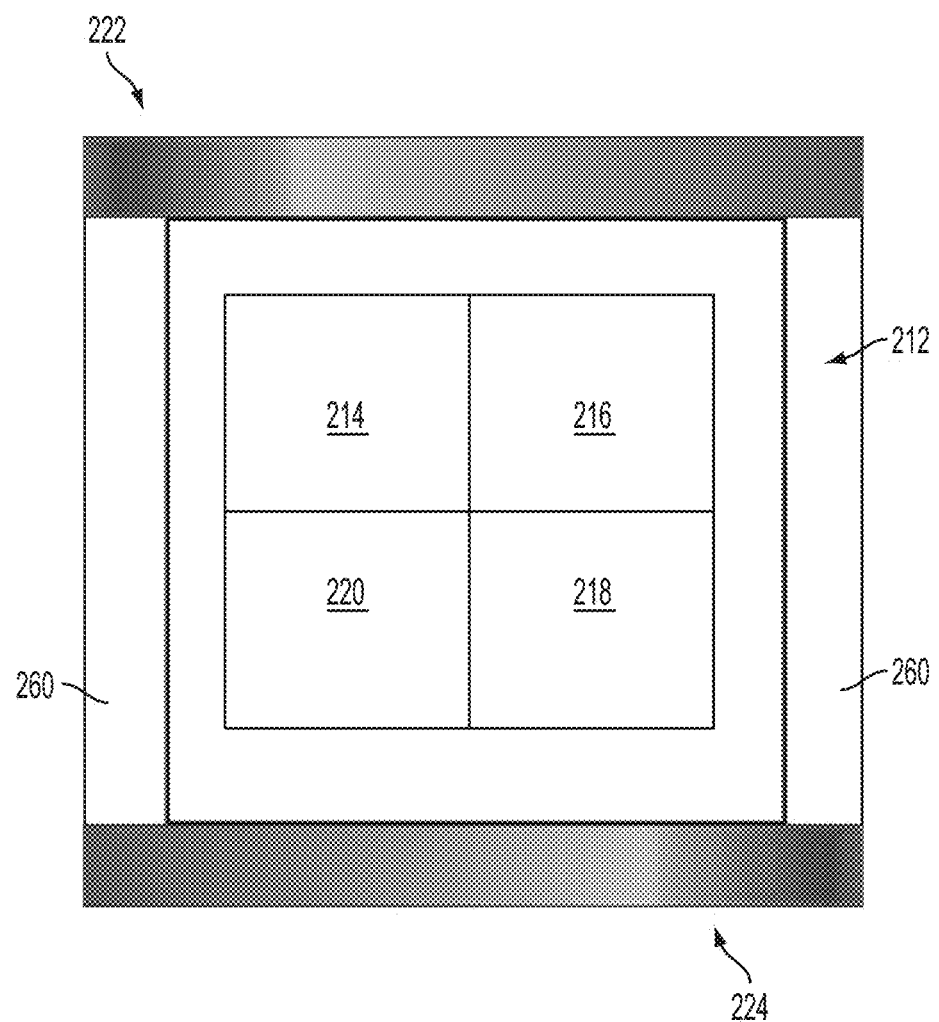
FIG. 9 is a plan view of a square substrate with four square regions and two color legends on opposite sides in accordance with another embodiment of the disclosure.

In FIG. 9, the testing device has a square substrate 212. Again, two color legends 222, 224 are placed on opposite sides of the substrate 212. Four rectangular analytical regions 214, 216, 218, 220 are present, each containing a reagent that reacts with the desired analyte to be tested for.

Figure 10:
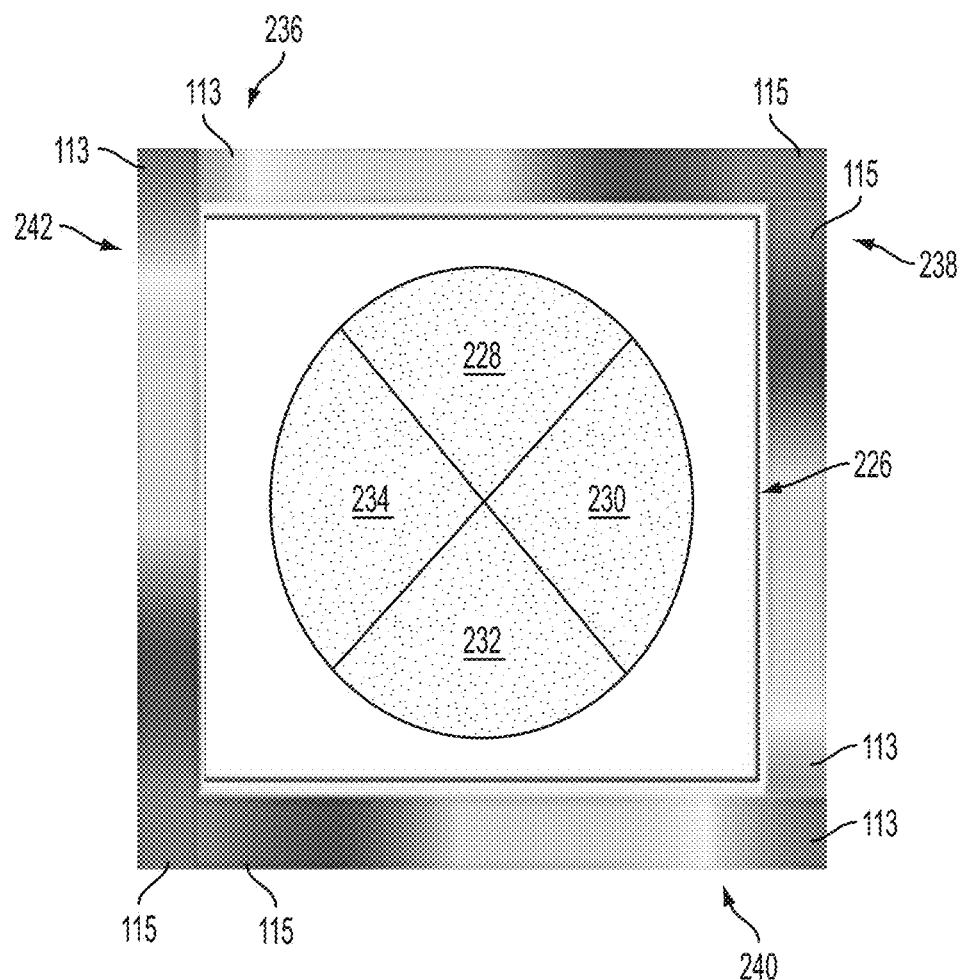
FIG. 10 is a plan view of a square substrate with four arcuate regions that together make a circle, and four color legends ranging in color from red to violet in accordance with another embodiment of the disclosure.

FIG. 10 illustrates a further embodiment of a testing device. The substrate 226 has a rectangular shape. Four color legends 236, 238, 240, 242 are present on the perimeter of the substrate. Here, each color legend has a color range from red to violet. The first ends 113 of each color legend are adjacent to the first end of another color legend, and the second end 115 of each color legend are adjacent to the second end of a different color legend. Again, four wedge-shaped analytical regions 228, 230, 232, 234 are present on the substrate within the color legends.

Figure 11:
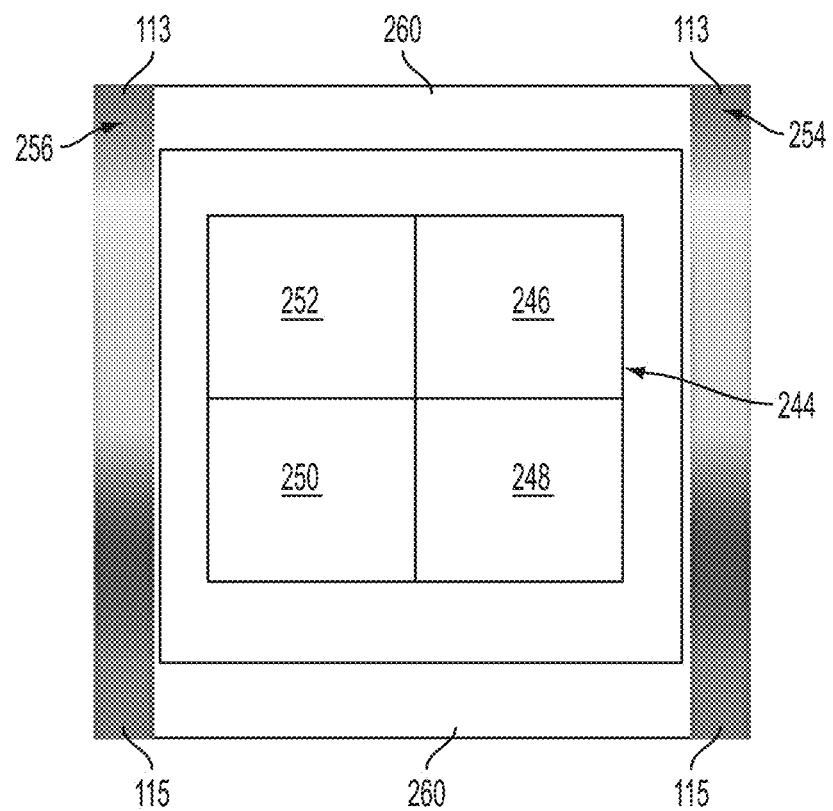
FIG. 11 is a plan view of a square substrate with four square analytical regions and two color legends ranging in color from red to violet in accordance with another embodiment of the disclosure.

FIG. 11 illustrates a further testing device wherein the substrate 244 has a rectangular shape. Here, only two color legends 254, 256 are present, located on opposite sides of the substrate 244. Four rectangular analytical regions 246, 248, 250, 252 are present on the substrate between the two color legends. The color legends for the testing device can range from red to violet or from red to green, corresponding to the possible resulting values of the reaction between analyte and reagent. Here, the first ends 113 of the two color legends are located at the same end of the substrate, and the second ends 115 are located at the same end of the substrate.

It is noted that in the various figures herein, the color legends either surround the analytical regions, or the analytical regions are located between the color legends. In some of the figures, the analytical regions are centered upon the substrate. However, in others, the analytical regions are offset to one end of the substrate. This may be useful in providing a handle or handling area where the user can manually hold the test unit, so that the user's fingers/hand are not present in the image that is captured by the imaging device. The handling area does not contain any color legend or analytical region or reagent, and in embodiments is located on one side of the substrate, along the perimeter of the substrate. Handling areas 260 are present in FIG. 9 and FIG. 11, and are located on a side of the substrate along the perimeter of the substrate. Only one handling area is needed, though each figure has two handling areas.

It is contemplated that in desired embodiments, the test unit includes multiple analytical regions, so that a multitude of samples can be analyzed at the same time. It is generally contemplated as well that the reagents in each analytical region are the same. This permits the color legends to be applicable to all of the analytical regions. Again, any bodily fluid, such as blood, urine, or saliva, can be placed on the substrate.

During the diagnostic process of using the test unit, capillary forces resulting from the microfluidic structure pull portions of the bodily fluid sample to the pre-deposited reagent, and a chemical reaction occurs. A change in color (i.e. color result) occurs if a specific analyte is present in the bodily fluid sample, for instance as a result of the concentration of the analyte. The color change can be captured and recorded by an imaging device such as a smart phone or camera phone.

Image analysis tools can then be used to convert the color result of each analytical region into a value for a desired property of the bodily fluid, such as the concentration of a given analyte. This imaging tool would be a camera on a smartphone, a tablet, or a laptop. The operator would proceed by taking the substrate on which the sample has been reacted to generate a color result, measuring the color result using an L*a*b* scanner, and then finding what value corresponds to the color result on the color legend.

A variety of different properties of the bodily fluid can be discerned by detecting a physical or chemical change through changes in color. For example, the LDL cholesterol level, pH value, the presence/level of glucose, or other biological properties may be detected using the testing device.

One advantage of the present disclosure is a higher degree of accuracy to the test administrators when returning results to a patient, because the test results can be more objectively measured along a numerical range. Another advantage of the present disclosure is that the method is efficient and allows a way to mass produce samples in a much higher volume than previously performed. The readings are also more precise and accurate, because the image analysis tool can compare the color result of the specific test against a color legend which is exposed to an uncalibrated camera in the same manner as the color result itself. Thus, any artifacts as a result of image processing will equally affect the color legend against which the color result is being compared.

The present disclosure has been described with reference to exemplary embodiments. Obviously, modifications and alterations will occur to others upon reading and understanding the preceding detailed description. It is intended that the present disclosure be construed as including all such modifications and alterations insofar as they come within the scope of the appended claims or the equivalents thereof.

The invention claimed is:

1. A diagnostic test unit for measuring a property of a bodily fluid, comprising:
    a hydrophilic substrate;
    a plurality of analytical regions on the substrate, wherein each analytical region includes a microfluidic structure made of a hydrophobic substance, each analytical region containing a reagent, wherein the reagent in each analytical region is the same; and
    a plurality of color legends on the substrate, wherein each color legend is the same, and each color legend comprising a color range corresponding to colors that can appear when the reagent reacts with an analyte, and each color legend having a first end and a second end; and wherein either:
    (A) the plurality of color legends forms a perimeter surrounding the plurality of analytical regions, wherein the first end of each color legend is placed adjacent to the second end of another color legend; or
    (B) the first ends of each color legend intersect at a common point on the substrate, and each analytical region is located between two color legends and a perimeter of the substrate.

2. The test unit of claim 1, wherein a total of four analytical regions are present on the substrate, and the four analytical regions are arranged in a rectangle.

3. The test unit of claim 1, wherein the substrate is rectangular, a total of four analytical regions are present on the substrate and arranged in a circle, and the test unit has a total of four color legends, wherein the four color legends form a perimeter surrounding the four analytical regions.

4. The test unit of claim 1, wherein the substrate is rectangular, and the test unit has a total of four color legends, wherein first ends of the four color legends intersect at a common point on the substrate.

5. The test unit of claim 1, wherein each color legend comprises a color range from red to violet, or from red to green.

6. The test unit of claim 1, further comprising a handling area on one side of the substrate.

7. A method of more accurately measuring a property of a bodily fluid, comprising:

receiving a test unit comprising a hydrophilic substrate, a plurality of analytical regions on the substrate, wherein each analytical region includes a microfluidic structure made of a hydrophobic substance, each analytical region containing a reagent, wherein the reagent in each analytical region is the same, and a plurality of color legends on the substrate, wherein each color legend is the same, and each color legend comprising a color range corresponding to colors that can appear when the reagent reacts with an analyte, and each color legend having a first end and a second end, and wherein either (A) the plurality of color legends forms a perimeter surrounding the plurality of analytical regions, wherein the first end of each color legend is placed adjacent to the second end of another color legend, or (B) the first ends of each color legend intersect at a common point on the substrate, and each analytical region is located between two color legends and a perimeter of the substrate;

placing a different analyte on each analytical region of the substrate;

permitting a reaction to occur;

capturing an image of each analytical region after the reaction with an imaging device; and comparing a color of each reacted analytical region in the captured image to at least one of the color legends in the captured image to determine a value for the property of the bodily fluid in each analytical region.

8. The method of claim 7, wherein the imaging device is a smart phone or tablet.

9. The method of claim 7, wherein blood, water, or saliva is a bodily fluid placed on each analytical region to react with the reagent.

10. The method of claim 7, wherein a pH value, a LDL cholesterol level, or a glucose level is the property of the bodily fluid that is measured.

11. The method of claim 7, wherein the substrate is rectangular, a total of four analytical regions are present on the substrate and arranged in a circle, and the test unit has a total of four color legends, wherein the four color legends form a perimeter around the four analytical regions.

12. The method of claim 7, wherein the substrate is rectangular, and the test unit has a total of four color legends, wherein first ends of the four color legends intersect at a common point on the substrate.

13. The method of claim 7, wherein each color legend comprises a color range from red to violet, or from red to green.

14. The method of claim 7, wherein the test unit further comprises a handling area on one side of the substrate.

* * * * *